(12) United States Patent
Hughes

(10) Patent No.: US 7,049,452 B2
(45) Date of Patent: May 23, 2006

(54) PREPARATION OF FATTY HYDROXAMATE

(75) Inventor: Terence Charles Hughes, Dandenong (AU)

(73) Assignee: Ausmelt Limited, Dandedong (AU)

( * ) Notice: Subject to any disclaimer, the term of this patent is extended or adjusted under 35 U.S.C. 154(b) by 404 days.

(21) Appl. No.: 10/351,697

(22) Filed: Jan. 27, 2003

(65) Prior Publication Data
US 2004/0059156 A1 Mar. 25, 2004

Related U.S. Application Data

(63) Continuation of application No. PCT/AU01/00920, filed on Feb. 27, 2002.

(30) Foreign Application Priority Data

| Jul. 28, 2000 | (AU) | .................................... PQ9068 |
| Oct. 3, 2000 | (AU) | .................................... PR0551 |

(51) Int. Cl.
*C07C 231/00* (2006.01)

(52) U.S. Cl. ........................................ 554/69
(58) Field of Classification Search ............ 554/69
See application file for complete search history.

(56) References Cited

U.S. PATENT DOCUMENTS

| 3,936,494 A | 2/1976 | Lipowski ............. 260/500.5 |
| 4,507,248 A | 3/1985 | Mathew et al. ......... 260/500.5 |
| 4,629,556 A | 12/1986 | Yoon et al. ............. 209/166 |
| 4,871,466 A | 10/1989 | Wang et al. ............... 252/61 |
| 4,929,343 A | 5/1990 | Wang et al. ............. 209/166 |
| 5,126,038 A | 6/1992 | Nagaraj .................. 209/166 |

FOREIGN PATENT DOCUMENTS

| EP | 0 311 759 B1 | 4/1989 |
| EP | 311759 | * 4/1989 |
| EP | 0 678 504 B1 | 10/1995 |
| WO | WO 02/10122 A1 | 2/2002 |

OTHER PUBLICATIONS

Supplementary European Search Report dated Sep. 21, 2005 for appl. EP 01 95 3679.
Shchukina, N.E. et al: "Synthesis of alkylhydroamic acids in an aqueous alkaline medium"; Zhurnal Prikladnoi Khimii (Sankt-Peterburg, Russian Federation), 45(8), 1895-7 Coden: Zpkhab: ISSN: 0044-4618, 1972, XP008052748; p. 1895, paragraph 4 and reaction scheme.
Database CA 'Online!; Chemical Abstracts Service, Columbus, Ohio, US; Shchukina, N.E. et al: "Synthesis of alkylhydroxamic acids in an aqueous alkaline medium"; XP002345746; retrieved from STN; Database accession No. 78:29193; abstract; & Zhurnal Prikladnoi Khimii (Sankt-Peterburg, Russian Federation), 45(8), 1895-7 Coden: Zpkhab; ISSN: 0044-4618, 1972, (Document cited in order to provide an abstract of the previous documents in the English language).
Vaysse L et al: "Fatty hydroxamic acid biosynthesis in aqueous medium in the presence of the lipase-acyltransferase from Candida parapsilosis"; Journal of Biotechnology, Elsevier Science Publishers, Amsterdam, NL, vol. 53, No. 1,28 Feb. 1997(1997-02-28), pp. 41-46, XP004094622; ISSN: 0168-1656; the whole document.

* cited by examiner

Primary Examiner—Deborah D. Carr
(74) Attorney, Agent, or Firm—Norris McLaughlin & Marcus PA

(57) ABSTRACT

A method for preparing fatty hydroxamic acids and salts thereof comprising reacting a fatty acid derivative with an aqueous solution of hydroxylamine.

19 Claims, No Drawings

PREPARATION OF FATTY HYDROXAMATE

This application is a continuation of PCT/AU01/00920 filed Feb. 27, 2002.

The present invention relates to a method for preparing salts and acids of fatty hydroxamates, to compositions containing salts of fatty hydroxamic acids and to a method of recovery of metals by a flotation process using the compositions.

BACKGROUND

Fatty hydroxamates are used as reagents in hydrometallurgical operations, particularly in froth flotation of oxidized minerals. The performance of fatty hydroxamates in such procedures is dependent upon the composition of the reagent. There is a need for an efficient method for producing fatty hydroxamates for industrial uses which provides reliable results.

SUMMARY OF THE INVENTION

The invention provides a method for preparation of fatty hydroxamic acids and salts thereof including reacting a fatty acid derivative with an aqueous solution of a hydroxylamine. The fatty acid derivative is preferably selected from the group of acid chlorides and esters. More preferably the fatty acid derivative is an ester selected from the group consisting of lower alkanol esters and glyceride esters. Hydroxylamine may be formed in situ from hydroxylamine salts in the presence of an alkaline aqueous solution which is typically an aqueous solution of alkali metal hydroxide. Alternatively hydroxylamine may be generated in situ from nitrosyl chloride or from ammonia in the presence of an oxidizing agent such as hydrogen peroxide.

During the reaction process the fatty hydroxamate which is formed generally produces foam. In the process of the present invention measures are preferably taken to suppress foam formation during the reaction. The reaction mixture may include a defoaming agent such as a lower alkanol or hydrocarbon. The defoaming agent is generally present in an amount of no more than 20% by weight of the reaction mixture and typically amounts of no more than 5% by weight of the composition are required.

Alternatively we have found that a foam suppressing agent is not required if the reaction is conducted under pressure. The amount of pressure required for effective foam suppression may vary between reaction mixtures and the skilled person will be able to determine the appropriate pressure for any system without undue experimentation. Typically, however a pressure generated during the reaction in the range of from 0.1 to 2 atmospheres may be sufficient. Foam may be adequately controlled in most instances by conducting the reaction in a sealed vessel. Alternatively a process for continuous preparation may use a tubular reactor kept under controlled pressurized conditions.

DETAILED DESCRIPTION OF PREFERRED EMBODIMENTS

It is a feature of the invention that the reaction is conducted in the presence of an aqueous solution of hydroxylamine in the presence of a strong base preferably consisting of an alkali metal hydroxide. In contrast to previous methods of preparing fatty hydroxamates the present invention allows the use of large amounts of organic solvent to be avoided and prepares the hydroxamate salt directly in the aqueous phase.

Until now it has been regarded as important to use the hydroxylamine in an organic solvent such as aliphatic alcohols as the reaction medium in order to obtain reaction of the hydroxylamine and fatty acid ester.

Hydroxylamine may be used in the form of an amine salt such as hydroxylammonium chloride or hydroxylammonium sulfate. In an alkali metal hydroxide solution the amine salts produce reactive hydroxylamine. It is particularly preferred to use hydroxylammonium sulfate as it is more readily available and preparation of the chloride is generally from the sulfate. The formation of the free hydroxylamine solution is carried out in glass or inert plastic lined equipment. The free hydroxylamine concentration is maintained at levels below 10% and the reactive hydroxylamine solution is used directly after removal of the precipitated alkali sulfate.

In one embodiment of the invention hydroxylamine or its salts are prepared from nitrosyl chloride in the presence of UV radiation:

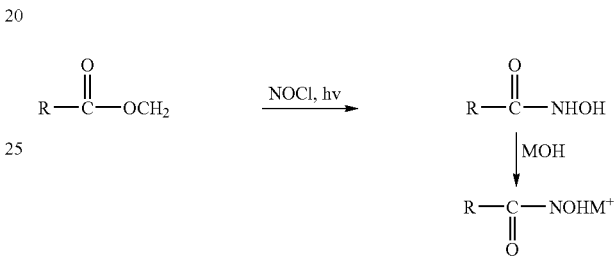

A further oximation process which generates hydroxylamine in situ involves the oxidation of ammonia using an oxidant, particularly hydrogen peroxide:

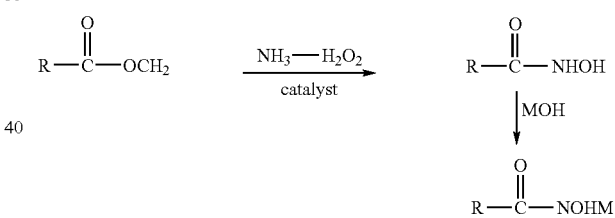

wherein M is an alkali metal such as sodium or potassium and R is fatty alkyl. The process of oximation of the fatty acid ester using ammonia and peroxide generally uses a catalyst. The catalyst is preferably selected from catalysts containing titanium and silicon. Preferably the catalyst has a zeolite structure. This oximation process may involve a pre-treatment of the catalyst with hydrogen peroxide.

The fatty hydroxamate is prepared using a fatty acid derivative. The fatty acid derivative may be a fatty acid chloride or an ester such as a lower alkanol ester of glyceride. The glyceride may be a mono-, di- or tri-glyceride.

The fatty hydroxamate is preferably prepared using a lower alkanol ester of fatty acid. The ester is typically a $C_1$ to $C_4$ alkanol ester of a fatty acid having from 6 to 18 carbon atoms. Preferably the alkanol portion of the ester is methyl or ethyl. The fatty acid portion of the fatty acid derivative may include one or more fatty acids. The most preferred fatty acid composition has a high concentration of fatty acids in the $C_6$ to $C_{14}$ range and most preferably the $C_8$ to $C_{10}$ range. The fatty acid component of the ester preferably contains 95% w/w of $C_6$ to $C_{14}$ and preferably at least 80% w/w of $C_8$ to $C_{10}$ fatty acids. Most preferably at least 95% w/w of the fatty acid component is made up of $C_6$ to $C_{10}$ fatty acids or a mixture thereof. Fatty acids in this range may be prepared by fractionation of an oil containing a high proportion of $C_8$–$C_{10}$ acids such as coconut oil and palm kernel oil.

The methyl ester of fractionated coconut oil is a preferred material for preparation of "Fatty Hydroxamate". Coconut methyl ester is preferably enriched with a $C_8$ and $C_{10}$ fraction in the composition ratio of 60:40 respectively.

Methyl ester of fractionated palm kernel oil can also be converted into a fatty hydroxamate material with characteristic flotation properties. Palm kernel oil contains a $C_8$ to $C_{10}$ composition similar to coconut oil Straight palm oil comes from a different part of the plant and is a less suitable composition of the $C_8$ and $C_{10}$ fraction than palm kernel oil.

We have also found that glycerides from coconut or palm kernel oil, like methyl ester, are reactive to free hydroxylamine and lead to the formation of fatty hydroxamate. The advantage of this process is that it allows the use of glyceride feed stocks from fractionated coconut or palm kernel oil into fatty hydroxamate without the intermediate reaction steps of transesterification, or saponification followed by esterification.

The most preferred glycerides are di or tri-glycerides with a high proportion of $C_8$ and $C_{10}$ fatty acid chains attached with glycerol site. Most of the fatty acid component is made up of $C_8$ and $C_{10}$ fatty acids or a mixture thereof.

Suitable carboxylic acids can also be derived from petrochemical sources. In this case the acids will most likely have a branched carbon chain structure rather than the straight carbon chain in natural fatty acids.

Examples of suitable petrochemical based carboxylic acids are: $C_8$-cekanoic acid (essentially iso-octanoic acid), 2-ethyl hexanoic acid, $C_9$-cekanoic acid (essentially 3,5,5-trimethyl hexanoic acid) and neo-decanoic acid (mixture).

Petrochemical derived alkyl ($C_8$–$C_{16}$) hydroxamates have been shown to have similar flotation advantages to that of natural $C_8$ and $C_{10}$ fatty hydroxamate.

It is found that the reactivity of cekanoic methyl ester especially those having a significant proportion of α-branching are less reactive to hydroxylamine. With derivatisation into acid chloride instead of ester, the reactivity of cekanoic acid toward free hydroxylamine is enhanced. Examples of α-branching fatty acids are $C_8$-cekanoic, 2-ethyl-hexanoic and neo-decanoic acids which, after conversion into their corresponding acid chloride, react effectively with hydroxylamine to give fatty hydroxamate.

Suitable carboxylic acids can also be derived from petrochemical sources, in this case the acids will probably have a branched carbon chain structure rather than the straight carbon chain in natural fatty acids. Examples of suitable petrochemically derived carboxylic acids are $C_8$ cekanoic acid (essentially iso-octanoic); ethyl hexanoic acid, neo-decanoic acid (mixture), $C_9$ cekanoic acid (essentially 3.5.5 tri methyl hexanoic acid).

We have found that fatty hydroxamates derived from $C_8$ to $C_{10}$ fatty acids provide particularly effective froth flotation collectors. They have been found to produce reagents of great flotation selectivity and recovery for oxidised base metals such as, but not exclusively, Cu, Pb, Zn, Ni, Co and Sn such as the sulfides or oxide based ores or the naturally occurring metals Cu, Ag, Au and platinum group metals when these metals occur in ores, tailings or wastes.

Petrochemical derived alkyl ($C_8$–$C_{16}$) hydroxamates have been shown to have similar flotation advantages to the $C_8$, $C_{10}$ potassium fatty hydroxamates.

In the preferred embodiment of the invention the alkali metal hydroxide is preferably sodium hydroxide or potassium hydroxide and potassium hydroxide is particularly preferred. The alkali metal hydroxide is generally present in an excess on a molar basis when compared with the amount of hydroxylamine component. Preferably the hydroxylamine component is present in an excess on a molar basis when compared with the amount of fatty acid ester. We have found that particularly good results are obtained when the molar ratio of fatty acid ester to hydroxylamine compound is in the range of 4 to 1.1 and preferably from 2.5 to 1.2. The molar ratio of alkali metal hydroxide to fatty acid ester is preferably in the range of from 4 to 1.5 and more preferably from 3.5 to 2.

The aqueous solution of alkali metal hydroxide will typically have a concentration in the range of 5 to 50% by weight and preferably from 10 to 25% by weight.

The method of the invention will preferably include agitating the reaction mixture to produce mixing of aqueous alkaline and fatty ester organic phases. Suitable mixing apparatus such as an impeller or the like may be used to produce mixing of an aqueous alkaline phase comprising the hydroxylamine and a water insoluble fatty acid ester phase. After a period of stirring a homogeneous mixture is generally formed.

Formation of the fatty hydroxamate may be accompanied by the formation of foam which may be maintained at an acceptable level by the antifoaming agent or by conducting the reaction under pressure. When used the antifoaming agent may be a lower alcohol such as methanol, ethanol or isopropanol or hydrocarbon solvent such as turpentine, diesel, kerosene or aviation fuel. The antifoaming agent is preferably present in an amount of less than 5% and most preferably less than 3% by weight of the total composition.

The reaction process is generally carried out at a temperature of from ambient to 90°. Relatively mild temperatures of up to 60° C. and more preferably 35 to 55° C. are used.

In contrast to many previous processes we have found that the addition of surfactants to the reaction mixture is unnecessary and undesirable. While some method of forming hydroxamate derivatives have been reported using fatty alcohols and/or other surfactant additives we have found that these additives generally suppress flotation performance of the hydroxamates formed in accordance with the present invention. Accordingly the reaction mixture preferably contains less than 0.5% by weight of added surfactant and most preferably is free of added surfactant. The added surfactant component does not include derivatives of the fatty acid ester component which may be formed as a result of the manufacturing process of the fatty acid esters. However it is preferred that the fatty acid ester has a purity at least 98% by weight.

We have found that the formation of the first small amount of fatty hydroxamate during the reaction procedure assists in mixing of the aqueous alkaline and organic phases to provide a homogenous composition and the hydroxamate may act as a surfactant and/or phase transfer agent to enhance faster reaction.

The fatty hydroxamate salt produced in accordance with the invention will typically exhibit absorption at approximately 3213, 1628 and 1554 $cm^{-1}$ due to the presence of organic hydroxamate group. In UV visible analysis it typically exhibits strong absorption of 499 nm after colour complexation with Fe III at pH 2–3.

The fatty hydroxamates particularly as the K salt may be used to produce froth flotation concentrates from base metal ores and tailings and provide high levels of recovered metal. The fatty hydroxamates can be used alone if only metal oxides or carbonates (eg. $SnO_2$-cassiterite $Cu_2O$-cuprite, $Cu_2(CO_3)(OH)_2$-malacite) are present, and are preferably used together with sulfide collectors (eg. xanthates or organo thiophosphates) if a mixture of sulfides and oxidised minerals is present, eg. Cu as chalcopyrite or chalcocite (fresh or oxidised), or as Cu oxides, carbonates, hydroxides or silicates (chryscolla). Metallic Cu, usually tarnished, silver, gold and platinum group metals are also recovered efficiently. A synergistic result appears with the mixed reagents (eg. xanthate plus fatty hydroxamate). For optimum performance and selectivity the fatty hydroxamate is used at pH 8.5 to 10.5 at low dose rates with a standard flotation frother.

The invention further provides a method of froth flotation including combining a fatty hydroxamate in the form of an alkali preferably potassium metal salt with an ore slurry and preferably a frothing agent.

The concentration of the alkali metal hydroxomate is typically in the range of 10 to 1000 mg per liter but will depend on the grade and amount of ore and the metals of interest. In terms of the quantity of ore the amount of alkali metal hydroxamate is generally in the range of 0.1 to 500 g per tonne but will of course also be highly dependent of these factors.

We have found that the efficiency recovery of particular metals by the flotation method is highly dependent on pH. Recovery of copper and many other metals is enhanced when the pH of the flotation liquor is no lower than 0.5 units less than the pKa of the Bronstead acid corresponding with the fatty hydroxamate. The pH may be higher than the pKa. The recovery of copper using potassium fatty hydroxamates is enhanced significantly when the pH is at least about 8.5 and more preferably from 8.5 to 10.5. In the case of tin however the optimum pH is typically acidic for example from pH 4 to 5 and this relationship of effectiveness of flotation with pKa is not observed.

The invention will now be demonstrated by, but is in no way limited to, the following examples.

EXAMPLE 1

Potassium salt of $C_8/C_{10}$ hydroxamate derivatives from coconut methyl ester. Hydroxylammonium sulfate (11.6 g, 0.14 mole equivalent of $NH_2OH$) was first treated with (16.06 g, 0.25 mole) KOH in 50 ml distilled water to generate free hydroxylamine reagent. The formation of by-product $K_2SO_4$ as precipitate, if necessary, could be easily separated by filtration or slow decantation of liquid reagent. The resulting free hydroxylamine solution in water (7–8%) was immediately reacted with methyl ester of coconut oil (20 g, 0.112 mole equivalent of $CO_2CH_3$) at 45° C., when agitated by an overhead mechanical stirrer. In order to control the foam rise generated from the reaction, 0.5 g of methanol was introduced as an antifoaming agent. After a stirring period of 6 hours the reaction mixture was exposed to air to allow the solvent to gradually evaporate to dryness. The resultant white, crude solid was subjected to an extraction process using warm methanol (4×20 ml) that allows separation of the hydroxamate salt from $K_2SO_4$ or any other inorganic impurities. The hydroxamate derivative contained in the methanol extract is finally recovered as a bright white powder by a typical crystallisation process (in other words, by distilling off the methanol as a solvent recycling procedure). After being left on a bench top to dry for 2 to 3 days a 17 g yield of white solid was obtained. This product appeared visually identical to the hydroxamate derivative produced when using methanol as a solvent. Its FT-IR spectral characterisation is summarised in Table 1.

EXAMPLE 2

Sodium salt of $C_8$–$C_{10}$ hydroxamate derivatives from coconut methyl ester. Following the identical procedure of Example 1, NaOH (10.28 g, 0.252 mole OH) was used as a base to generate the hydroxylamine reagent. Unlike potassium salt, the sodium salt of hydroxamate appears to be hygroscopic. Its yield of 12 to 15 g after crystallisation from methanol falls in the same range as its corresponding potassium salt. Its FT-IR spectral pattern, as seen in Table 1, also displays a close similarity to that seen from the typical hydroxamate derivative produced in a methanol solvent.

FT-IR Analysis

Following the standard KBr disc method it was found that samples of both the sodium and potassium salt described above comprised a characteristic hydroxamate functional group. As shown in Table 1, the potassium fatty hydroxamate (AM2) derived from present route (i.e. in water and using hydroxylammonium sulfate salt) produced virtually the same diagnostic signal as AM2 that was made via a methanol solvent route. The amide carbonyl peaks at 1627 and 1554 $cm^{-1}$ due to keto-enol tautomers, accompanied with strong hydroxyl (—OH) stretching vibration at 3213 $cm^{-1}$, which supports the conclusion that a hydroxamate function (—$CONOH^-K^+$) is present in the product. The sodium salt form also shows similar signals, albeit giving a different frequency. This may be partly due to a different counter cation binding effect with conjugate hydroxamate function. It is known that cation size (ionic radii) has an effect on ion-pair stability as shown above structural form.

TABLE 1

$$R-C(=O)-NOH^- K^+ \quad\quad R-C(=O)-NOH^- Na^+$$

| Sample material | IR signals at wave number ($v\ cm^{-1}$) | |
| --- | --- | --- |
| Solid AM2 made from coconut methyl ester by methanol solvent method | 1627 and 1554 (carbonyl from amide) | 3213.5 (—OH) |
| Potassium salt of AM2 made by present method | 1627.4 and 1554 (carbonyl) | 3213.2 (—OH) |
| Sodium salt of AM2 made by present method | 1633 and 1574 (carbonyl) | 3244 (—OH) |

EXAMPLE 3

The procedure of Example 1 was repeated with the exception that the defoaming agent, methanol was omitted and the reaction was carried out in a sealed pressure vessel. The pressure vessel was lined with "Teflon" fluoropolymer and supported by a stainless steel shell and clamp. The pressure vessel was filled to a level of 70% to generate a vapour pressure during the reaction which was found to suppress foam formation during the reaction.

The progress of the reaction may be monitored by FTIR by monitoring the region between 1000 and 4000 $cm^{-1}$. As the reaction progresses the concentration of the ester carbonyl will gradually diminish. This can be observed by a similar reduction in height of the characteristic ester carbonyl FTIR peak at wavelength 1739 $cm^{-1}$.

The liquid potassium salt of the fatty hydroxamic acid is transformed into a white solid upon cooling and evaporation of the water solvent. The physical and chemical properties closely resemble the product of Example 1

EXAMPLE 4

Potassium salt of $C_8/C_{10}$ hydroxamate derivatives from coconut oil. A 7–8% free hydroxylamine reagent was generated by following a procedure similar to than in Example 1. It was then immediately reacted with triglyceride of coconut oil (22.5 g, saponification value 279, 0.112 mole equivalent of glyceride) at 45° C., under agitation. After a stirring period of 12 hours the white, creamy material was transferred to a pyrex bowl and was exposed to air to allow the solvent to gradually evaporate to dryness. The resultant white, paste product was subjected to washing with cold methanol to remove glycerol and other organic materials. The FTIR spectrum of dry white powder (18 g) showed an absorption band similar to that of the potassium salt of $C_8/C_{10}$ hydroxamate derivative made in Example 1.

EXAMPLE 5

$C_9$-cekanoic Hydroxamic Acid.

A 7–8% free hydroxylamine reagent, generated by following Example 1, was reacted with methyl ester of $C_9$-cekanoic acid (19.7 g, 0.112 mole equivalent —$CO_2CH_3$) in a glass reactor using similar reaction conditions as described in Example 1. Unlike the product of $C_8$ and $C_{10}$ coconut fatty hydroxamate, the $C_9$-cekanoic hydroxamate product appeared as a clear homogeneous liquid. Upon acidification with 1 M HCl a white precipitate of $C_9$-cekanoic hydroxamic acid was formed. After filtration, water wash and air dry at 15 g of white powder of cekanoic hydroxamic acid was obtained.

EXAMPLE 6

A 1 kg sample of the mineral feedstock was ground to 80% less than 75 μm and was subjected to standard flotation methods in a 2 liter laboratory flotation cell. The fatty hydroxamate was added as required, either as the solid or dispersed in warm water at 0.1 to 500 g/tonne at a pH 8 to 10.5 or warm 1% potassium hydroxide solution. Methyl isobutyl carbinol (MIBC) was used as required as a frother (up to 10 g/tonne). The composition of the froth concentrate defined is shown in the table below.

| Feedstock and Metal Content | | Flotation Concentrate Content |
| --- | --- | --- |
| Supergene Cu ore | Cu 0.6% | Cu 12% |
| Oxidised Cu ore | Cu 0.8% | Cu 38% |
|  | Au 0.9 ppm | Au 12 ppm |
| Oxidised Zn ore | Zn 2.5% | Zn 15.5% |
| $SnO_2$ tailings | Sn 0.6% | Sn 9.5% |

The invention claimed is:

1. A method for preparing fatty hydroxamic acids and salts thereof comprising forming a two phase system including a water insoluble phase comprising a lower alkanol ester of a fatty acid which phase is essentially free of organic solvents, and an aqueous phase comprising hydroxylamine and, mixing the phases to provide reaction of the lower alkanol ester of the fatty acid and the hydroxylamine to form a fatty acid hydroxamic acid or salt thereof.

2. A method according to claim 1 wherein the two phases are essentially free of added surfactant.

3. A method according to claim 2 wherein hydroxylamine is formed in situ from hydroxylamine salts in the presence of an alkaline aqueous solution.

4. A method according to claim 2 wherein hydroxylamine is formed in situ from nitroxyl chloride or ammonia in the presence of an oxidizing agent.

5. A method according to claim 1 wherein the reaction mixture comprises no more than 5% wt. of added lower alkanol defoaming agent.

6. A method according to claim 1 wherein the reaction produces foam under ambient conditions and the method further includes conducting the reaction under a pressure sufficient to suppress foam formation.

7. A method according to claim 6 wherein the reaction is conducted under a pressure in the range of from 0.1 to 2 atmospheres.

8. A method according to claim 6 wherein the reaction in conducted in a tubular reactor.

9. A method according to claim 3 wherein hydroxylamine is formed in situ from one or more of hydroxylammonium chloride and hydroxylammonium sulfate.

10. A method according to claim 1 wherein the fatty acid derivative is selected from the group consisting of $C_1$ to $C_4$ alkyl esters of fatty acids, fatty acid chlorides and mono-, di- and tri-glycerides of fatty acids.

11. A method according to claim 1 wherein the fatty acid component of the fatty acid derivative comprises at least 95% by weight of $C_6$ to $C_{14}$ fatty acids.

12. A method according to claim 1 wherein the fatty acid component of the fatty acid derivative comprises at least 95% by weight of $C_6$ to $C_{10}$ fatty acids.

13. A method according to claim 3 wherein the hydroxylamine is reacted with the lower alkanol ester of the fatty acid in the presence of an aqueous alkaline solution selected from sodium hydroxide and potassium hydroxide and the resulting product is a hydroxamic acid salt formed with a counter ion selected from sodium and potassium.

14. A method according to claim 13 wherein the alkali metal is potassium hydroxide.

15. A method according to claim 13 wherein the aqueous alkaline solution comprises a concentration of sodium hydroxide or potassium hydroxide in the range of from 5 to 25% by weight.

16. A method according to claim 1 wherein the reaction is carried out at a temperature in the range of from 35 to 55° C.

17. A method according to claim 1 wherein the fatty acid component of the fatty acid derivative comprises one or more branched fatty acids.

18. A method according to claim 14 wherein the branched fatty acid is a $C_8$–$C_{16}$ fatty acid.

19. A method according to claim 18 wherein the fatty acid is selected from the group consisting of iso-octanoic acid, 2-ethyl hexanoic acid, iso-nonanoic acid and neo-decanoic acid.

\* \* \* \* \*